(12) United States Patent
Liu

(10) Patent No.: US 9,440,069 B2
(45) Date of Patent: Sep. 13, 2016

(54) PERCUTANEOUS CONTINUAL ELECTRO-ACUPUNCTURE STIMULATION FOR IN VIVO AND IN SITU TISSUE ENGINEERING

(75) Inventor: Y. King Liu, Petaluma, CA (US)

(73) Assignee: Y. King Liu, Petaluma, CA (US)

( * ) Notice: Subject to any disclaimer, the term of this patent is extended or adjusted under 35 U.S.C. 154(b) by 618 days.

(21) Appl. No.: 12/626,034

(22) Filed: Nov. 25, 2009

(65) Prior Publication Data

US 2010/0137939 A1 Jun. 3, 2010

Related U.S. Application Data

(63) Continuation of application No. 11/747,075, filed on May 10, 2007, now abandoned.

(60) Provisional application No. 60/799,263, filed on May 10, 2006.

(51) Int. Cl.
*A61N 1/36* (2006.01)
*A61N 1/05* (2006.01)
*A61N 1/32* (2006.01)

(52) U.S. Cl.
CPC ......... *A61N 1/36021* (2013.01); *A61N 1/0502* (2013.01); *A61N 1/321* (2013.01); *A61N 1/326* (2013.01); *A61N 1/36017* (2013.01)

(58) Field of Classification Search
CPC .................................................. A61N 1/36017
USPC ........................................................... 607/50
See application file for complete search history.

(56) References Cited

U.S. PATENT DOCUMENTS

| 5,211,184 | A | * | 5/1993 | Yee et al. ....................... 607/149 |
| 6,549,810 | B1 | * | 4/2003 | Leonard et al. ............... 607/115 |
| 2004/0044390 | A1 | * | 3/2004 | Szeles ........................... 607/142 |

* cited by examiner

*Primary Examiner* — Eric D. Bertram
(74) *Attorney, Agent, or Firm* — Suganda Jutamulia

(57) ABSTRACT

The invention includes an electro-acupuncture stimulation system for in vivo and in situ analgesia and tissue repair and regeneration. Electrodes, which can be acupuncture needles, are percutaneously implanted that deliver a pulsed electrical current that creates an electrical field, which envelopes the targeted tissue and restores cell-generating homeostasis to the affected tissue and thereby promotes analgesia and tissue re-growth in otherwise debilitated or deteriorating tissue. Methods and apparatuses are also disclosed that may include a needle locking system and acupuncture-needle assemblies for long-term in situ electrical stimulation.

9 Claims, 7 Drawing Sheets

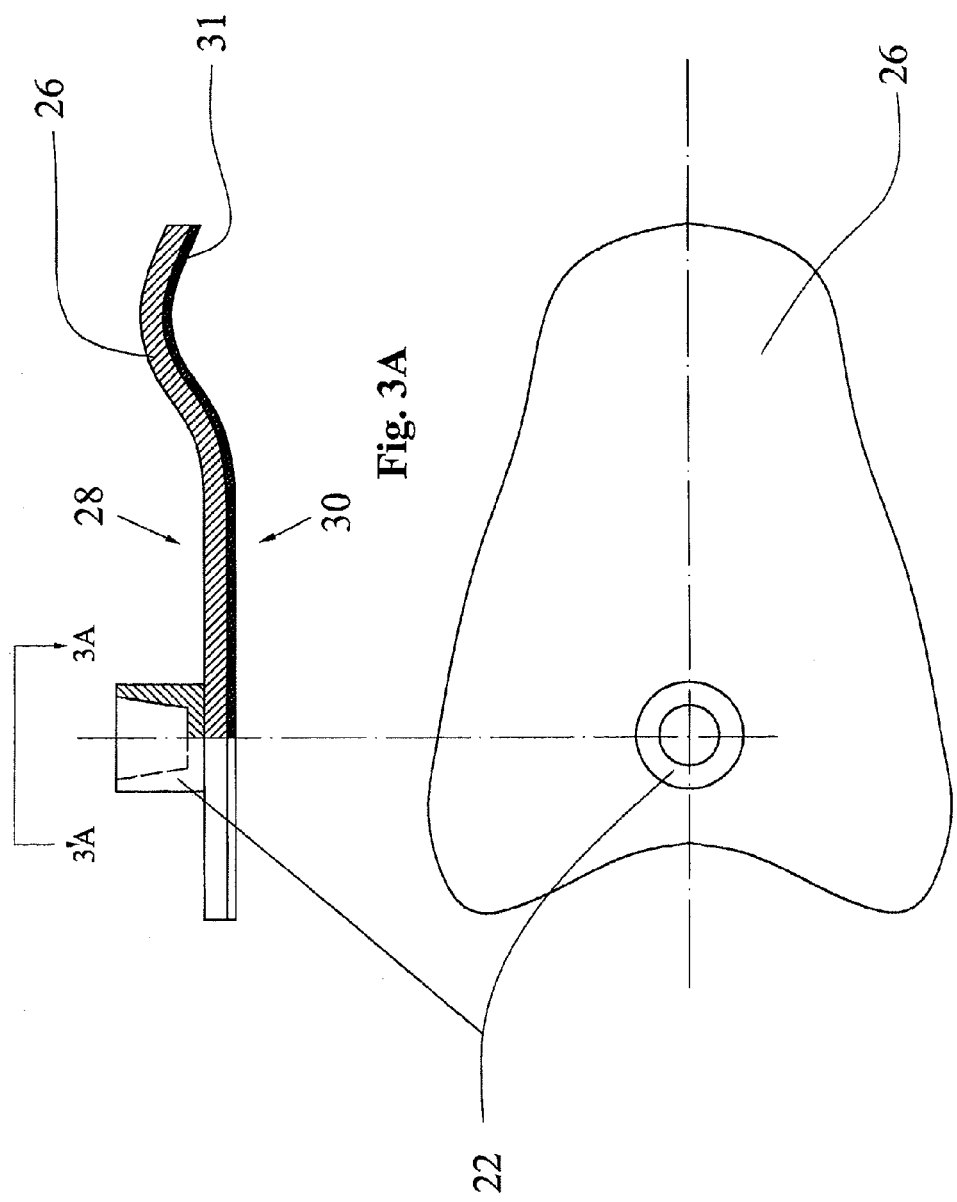

PERCUTANEOUS CONTINUAL ELECTRO-ACUPUNCTURE STIMULATION FOR IN VIVO AND IN SITU TISSUE ENGINEERING

CROSS-REFERENCE TO RELATED APPLICATIONS

This application claims priority under 35 U.S.C. §120 as a continuation application of U.S. patent application Ser. No. 11/747,075 filed on May 10, 2007, which in turn claims priority under 35 U.S.C. §119 to U.S. Provisional Application No. 60/799,263, filed May 10, 2006. The disclosure of both priority applications is hereby incorporated by reference in their entireties.

BACKGROUND OF THE INVENTION

In China, the insertion of acupuncture needles into acupuncture points to treat diseases has been practiced for at least 2,000 years. The addition of electricity or electro-acupuncture was documented in a French text as early as in 1825. Its author, Chevalier Solardiere, claimed that when static electricity, generated by rubbing a silk scarf against ebony was discharged into the inserted acupuncture needles, the electrical discharge enhanced the therapeutic results of acupuncture. In the 1950's, Chinese acupuncture practitioners used an automobile starter motor as a continuous source of electrical stimuli to acupuncture needles to enhance the efficacy and efficiency of the acupuncture therapeutic effects. Since that original motor-starter stimulator, various electronic stimulators have been employed with a plethora of therapeutic claims. The stimuli delivered by these stimulators to the acupuncture points through the acupuncture needles have varied in frequency, voltage, current, pulse shape and duration. The duration of the electrical stimuli is generally very brief, such as ranging from 10 to 60 minutes. One such system and method can be found in U.S. Pat. No. 7,200,444 to Gavronsky et al., herein incorporated by reference in its entirety. To Applicants' knowledge, none have sought to percutaneously implant the acupuncture needles for a prolonged period of time. This invention describes such a system.

FIELD OF THE INVENTION

This invention relates to electro-acupunctural stimulation and more specifically to percutaneous nearly continual electrical stimulation of appropriately inserted acupuncture needles to specific known anatomical and acupuncture points to achieve certain in vivo and in situ therapeutic effects on analgesia and tissue regeneration and repair.

SUMMARY OF THE INVENTION

According to one embodiment of the invention, disclosed is an electro-acupuncture system, in which the acupuncture needles are percutaneously implanted through an acupuncture guide tube. The shank of a specially designed and constructed acupuncture-needle is a male screw thread. Once the needle is in place, a small hollow cylinder with a corresponding female thread in the inside diameter is used to fixate an antibacterial O-ring against the skin to prevent infection. The O-ring is placed in a cutout at one end of the hollow cylinder while the other end has a tapered section with rings and longitudinal sections trisecting the rings perpendicularly. A plastic winged butterfly fixture is molded to consist of a bendable piece of soft plastic with pieces of wire embedded as flexible reinforcement. Velcro is attached to one side of the butterfly surface. Near the tail of the other side of the butterfly is a metallic cup. The metallic cup has a slightly tapered internal inside diameter so that the shank of the implanted needle can be interference-fitted to the cup. A small wire is tied and soldered solidly to the cup and is then connected to an electrical stimulator. Both sides of the electrical stimulator are fitted with Velcro. In this fashion, when all the needles are fixated and in place, a double sided Velcro band is used to secure all the plastic butterflies snugly. The electrical stimulators are affixed to the first Velcro band. A one-sided Velcro band is then wrapped around the first band to complete the installation.

In some embodiments, disclosed is a customized electrode in-dwelling stimulation assembly. This assembly is embodied in an expandable sleeve that form-fits over the knee and is secured with Velcro fixations. The assembly includes a battery-powered miniature electrical stimulator and is housed with butterfly snaps and wire leads that attach to a set of pre-inserted electrodes that allow the delivery of electrical stimulus, which envelopes joint cartilage within a custom tissue repairing electromagnetic field.

In one embodiment, disclosed is a securable percutaneous electro-acupunctural system that includes at least one needle comprising an elongate body, proximal end, and distal end, the needle having a fastener component disposed on the elongate body; and a needle-securing element configured to lock said implanted needles in situ. The needle is preferably retained in a desired anatomical landmark, such as an acupuncture point. In some embodiments, the elongate body of the needle comprises a male screw threaded portion. The needles can have a diameter of between about 30 to 34 gauge. The needles can have a length between about 8 mm to 2.5 cm. The needle-securing element can include a female-threaded portion that is configured to interface with the male threaded portion of the needle. The system can further include an O-ring at a distal end of the needle-securing element. The O-ring can include an antimicrobial agent. The needle-securing element can have a press-fit outer surface. The system can further include a fixator cup sized to at least partially cover the needle-securing element. The fixator cup can also include a press-fit inner surface configured to attach to the press-fit outer surface of the needle-securing element. In some embodiments, the outside surface of the cup is tied or soldered with a ring, which is connected to an insulated wire. The wire is connected to one of the positive or negative leads of a jack, the jack having both the positive and negative leads connected to it; the jack operably connected to an output port of an electronic stimulator. The system can also include a skin overlaying component having a first side and a second side, the skin overlaying component configured to fit over the fixator cup and the contour of surrounding skin of a patient over the first side of the skin overlaying component. The skin overlaying component can include embedded flexible wires to facilitate bending to fit the contour of the surrounding skin of a patient. The second side of the skin overlaying component can include fastener material. The system can also include an electrical stimulator. The electrical stimulator can be at least partially covered by a fastener material; the fastener material of the electrical stimulator configured to attach to the fastener material of the second side of the skin overlaying component. In some embodiments, the system further includes a strap with a first side and a second side; the first side of the strap comprising fastener material configured to attach to the fastener material of the electrical stimulator.

Also disclosed herein is a method of treating a patient. The method includes the steps of providing a plurality of needles; selecting one or more treatment sites on a patient; inserting the needles percutaneously into the treatment site of the patient; providing an electrical stimulator; connecting the needles to the stimulator, and activating the stimulator; wherein the needles remain percutaneously inserted in the treatment site for at least 24 hours. In some embodiments, the step of activating the stimulator involves increasing the power on the stimulator to a threshold level of sensation by the patient, and decreasing the power until it becomes sub-sensory to the patient. The treatment site can be a joint, such as a knee. In some embodiments, the treatment site comprises one or more acupuncture points selected from the group consisting of Heting (S156), Spleen 10, Stomach 34, Bladder 40, Stomach 35, and Hsiyen (S145). In some embodiments, the needles remain percutaneously inserted in the treatment site for at least a twenty-four hour period. The needles can be operably connected to a needle-securing element configured to keep the needle in its originally inserted position. The patient may exhibit signs and/or symptoms of osteoarthritis. The duration of the percutaneous electrical stimulus is governed by the severity of the osteoarthritis disease being treated. For example, Grade I osteoarthritis, might include electrical stimulus over the course of one week versus a treatment period of three or more weeks for Grade III osteoarthritis. For all treatments, clinical judgment will determine the duration of electrical stimulus period. In some embodiments, the treatment sites include the points Heting (S156), Spleen 10, Stomach 34, Bladder 40, Stomach 35, and Hsiyen (S145) and the needles inserted into the treatment sites Heting (S156), Spleen 10, and Stomach 34 serve as positive electrodes while the needles inserted into treatment sites Bladder 40, Stomach 35, and Hsiyen (S145) serve as negative electrodes. In some embodiments, the stimulator is activated for at least about 4 hours per day.

BRIEF DESCRIPTION OF THE DRAWINGS

The invention is further illustrated in the following Figures.

FIGS. 3A-B further illustrates the inter-relationship between the skin overlaying component and the fixator cup. In this illustration, the skin overlaying component is bent so as to fit the contours of the skin. This is also shown in FIG. 2.

DETAILED DESCRIPTION OF THE PREFERRED EMBODIMENT

Disclosed herein are devices and methods for analgesia and tissue repair and regeneration that does not require major surgery or a research-intensive stem cell approach and, at the same time, it is a minimally invasive fast-acting treatment. The disclosed treatment is inexpensive when compared to surgical treatments and faster acting than current non-invasive devices. This recent biomedical breakthrough is a vast improvement over current treatment modalities, whether measured by cost or by time-to-heal effectiveness.

According to some embodiments of the invention, disclosed is an externally implanted electrotherapeutic in-dwelling system for treating osteoarthritis including pain, joint stiffness, limitation of range of motion and limitation of overall function through the use of percutaneous sub-sensory unidirectional voltage or current pulses. The electrical stimulus can be applied, in one embodiment, through six 30-34 gauge needle electrodes inserted into the appropriate anatomical points of the patient such that it is close to the cartilaginous surfaces of an osteoarthritic joint. The electrotherapeutic stimulation restores the normal electromagnetic field enveloping the joint. For the cartilage tissue, the field stimulates chondrocyte functioning, and increases synthesis of proteoglycans and Type II collagen molecules in cartilage resulting in the efficient and efficacious repair of damaged cartilage. The devices and methods disclosed herein can be more efficient and efficacious than, for example, transcutaneous electrical stimulation through non-specifically placed surface electrodes. Articular cartilage and fibrocartilage repair can potentially take place after three to four weeks of continuous treatment.

Most current treatments for advanced arthritis, such as osteoarthritis involve surgically invasive interventions, such as total knee replacement or total hip replacement. These treatments are costly and for some they can be quite perilous in terms of patient morbidity and mortality. Post surgical recovery requires significant time and total joint replacement surgery presents complications or compromised functionality for about 10% of patients. There are few alternative treatments that have shown effectiveness compared to conservative as well as standard surgical practices. Those that do exist require months of treatment. To the contrary, the device and method shown can provide a fast-acting minimally invasive alternative treatment that works continuously or substantially continuously and, in most cases, will permit daily patient ambulation, which will further patient rehabilitation.

Figure 1B:
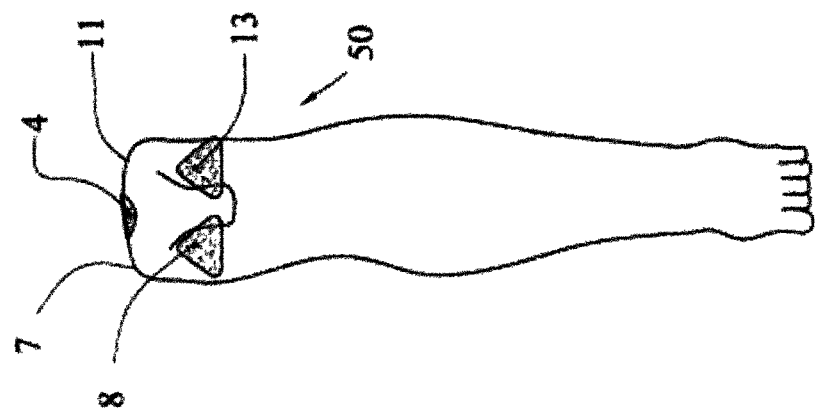
FIGS. 1A-1B show an overview of the acupuncture-needle assembly system applied to produce analgesia, repair and/or regeneration of cartilage in the knee joint.
Figure 1A:
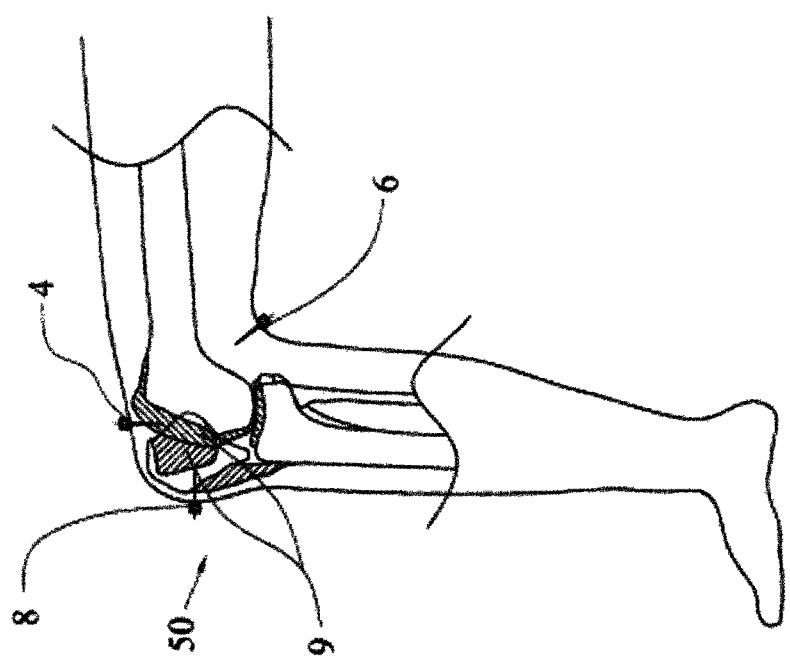

FIGS. 1A-1B illustrate some non-limiting possible advantageous locations to produce analgesia, repair and/or regeneration of cartilage 9 in the knee joint 50. FIG. 1A is a lateral schematic view of the knee 50 illustrating acupuncture needles inserted into the "Hsiyen (S145) point", also known as "eye of the knee" 8, "Heting point (S156)" 4, and "Bladder 40" 6. FIG. 1B is a frontal schematic view of the knee illustrating other advantageous acupuncture points for knee analgesia, repair, and/or regeneration of cartilage, such as "Hsiyen (S145) 8", "Spleen 10" 7, "Heting point (S156)" 4, "Stomach 34" 11, and "Stomach 35" 13. These points can be located by one of ordinary skill in the art as described below:

"Hsiyen (S145)" 8: Locate this point with knee flexed, at the lower border of the patella in the depression lateral to the patellar ligament.

"Stomach 34" 11: Locate this point with knee flexed, two finger-widths (comparable to the patients fingers size) above the mediosuperior border of the patella on the bulge of the medial portion of the quadriceps femoris muscle.

"Stomach 35" 13: Locate this point in the depression, medial to the patellar ligament, locating the point with the knee flexed.

"Spleen 10" 7: Locate this point with the knee flexed, measure two thumb widths (comparable to the patients thumb size) above the laterosuperior border of the patella.

"Heting (S156)" 4: Locate this point at the depression of the midpoint of the superior patellar border.

"Bladder 40" 6: Locate this point at the midpoint of the transverse crease of the popliteal fossa, between the tendons of the biceps femoris and semitendinosus muscles.

The nature and location of various points and meridians used in Chinese acupuncture are described in many texts, such as the following; the book "Acupuncture in Medical Practice", Louise O. Wensel, M.D., published 1980 by Reston Publishing (A Prentice Hall Company) is particularly noted; the book "Acupuncture, The Ancient Chinese Art of Healing and How it Works Scientifically", Felix Mann, M. B. published 1973 by Vintage Books, a division of Random House, New York; the book "Chinese Acupuncture and Moxibustion" Revised Edition, Chief Editor Cheng Xinnong published 1999 by Foreign Languages Press, Beijing, and; the book "A Manual of Acupuncture" by Peter Deadman et al. published 2001 by Journal of Chinese Medicine Publications. All of these four texts are herein incorporated by reference in their entirety. Appropriate corresponding anatomical landmarks can be selected in order to produce the desired clinical result.

An embodiment of the invention involves the fixation of an acupuncture needle into the body of a patient through a conventional guide tube. Some guide tubes usable with the present invention are described in U.S. Pat. No. 5,792,171 to Burdenko et al. and U.S. Pat. No. 6,231,584 to Gavronsky, which are incorporated by reference herein in their entirety. One embodiment of an acupuncture needle and system is illustrated schematically in FIG. 2. The needle 10 has a beveled distal tip 12 for ease of needle 10 insertion. The body 14, also referred to herein as the shank portion 14 of the needle 10, includes a locking element in some embodiments, preferably disposed on the outer diameter of the needle 10. The locking element is preferably a male screw thread. In other embodiments, the needle can be a conventional acupuncture needle with lengths and dimensions as known in the art or the needle can be incorporated into a needle cap assembly within the fixator cup 22 that houses the electrical lead from the electrical stimulator 34 that attaches to the upper shank portion 14 in the needle cap assembly within the fixator cup 22.

A practitioner will typically position a guide tube (not shown) over the skin 24, and then insert the needle 10 into the guide tube. There is typically about 3-5 mm clearance between the upper end of the guide tube and the top (proximal end) of the acupuncture needle 10, which protrudes above the tube. The practitioner can then tap on the proximal end of the needle 10 downward with an index finger while supporting the tube with the other fingers. The needle 10, which has been resting on the surface of the patient's skin prior to insertion, is now inserted 3-5 mm through the skin into the desired acupunctural anatomical point. The acupuncture needle used may be of any length and diameter, depending on the desired clinical result. In some embodiments, the needle is preferably between about 8 mm to 2.5 cm in length and no more than about 5 cm in length. The diameter of the needle is preferably between about 20 to 40 gauge, more preferably between about 28 to 36 gauge, more preferably between about 30 to 34 gauge.

Figure 2:
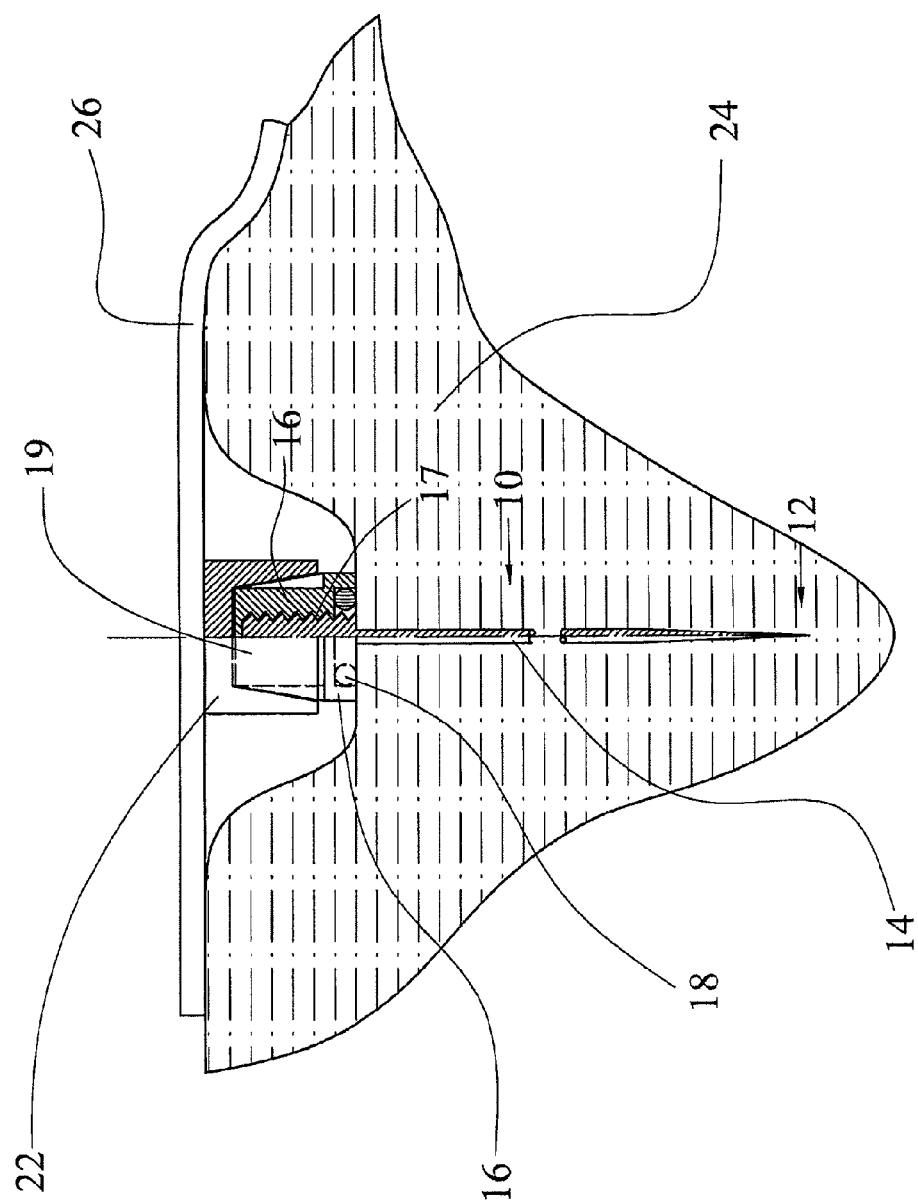
FIG. 2 illustrates how the percutaneous acupuncture-needle assembly is fixated against the skin, according to some embodiments of the invention.

As shown in FIG. 2, after insertion, with the help of the guide tube, a needle-securing element 16 configured to interface with the needle 10 is placed over the proximal end of the needle 10. In one embodiment, the needle-securing element 16 is a hollow tubular body, which may be a relatively short shank, approximately 3-6 mm in length, with a female screw thread lining the inner diameter of the needle-securing element 16. In other embodiments, the needle-securing element 16 could be a molded element integrally formed with the needle, an adhesive or other fastener, a lock, ratchet, etc. The female screw thread 17 of needle-securing element 16 is most preferably adapted to accommodate the male screw thread portion of the needle 10. The needle-securing element 16 also includes an O-ring 18 at its distal end in some embodiments. The needle-securing element 16 can be screwed in place and closed with a locked nut, in between fixator cup and needle-securing element 16. In some embodiments, at least a portion of the O-ring 18, such as the inner diameter portion can be coated or impregnated with an antimicrobial agent that is preferably broad-spectrum and/or covers skin organisms, in order to prevent infection of the needle insertion site. The proximal end 19 of the needle-securing element 16 preferably has a press-fit outer surface. Fixator cup 22 preferably also includes a press-fit surface on its inner surface configured to attach to the outer press-fit surface of the needle-securing element 16, such as by friction. The press-fit surfaces, in some embodiments, include criss-crossing shallow rings and ribs that can be perpendicular to one another.

A skin overlaying component, which is also referred to as a butterfly 26 fixture herein, can be preferably molded of a bendable piece of soft plastic. In some embodiments, wires can be embedded within the butterfly 26 as flexible reinforcement. The butterfly 26 can also be made of any biocompatible material known in the art, such as neoprene, polyurethane or other polymers, ePTFE, PTFE, Dacron, and the like.

Figure 2A:
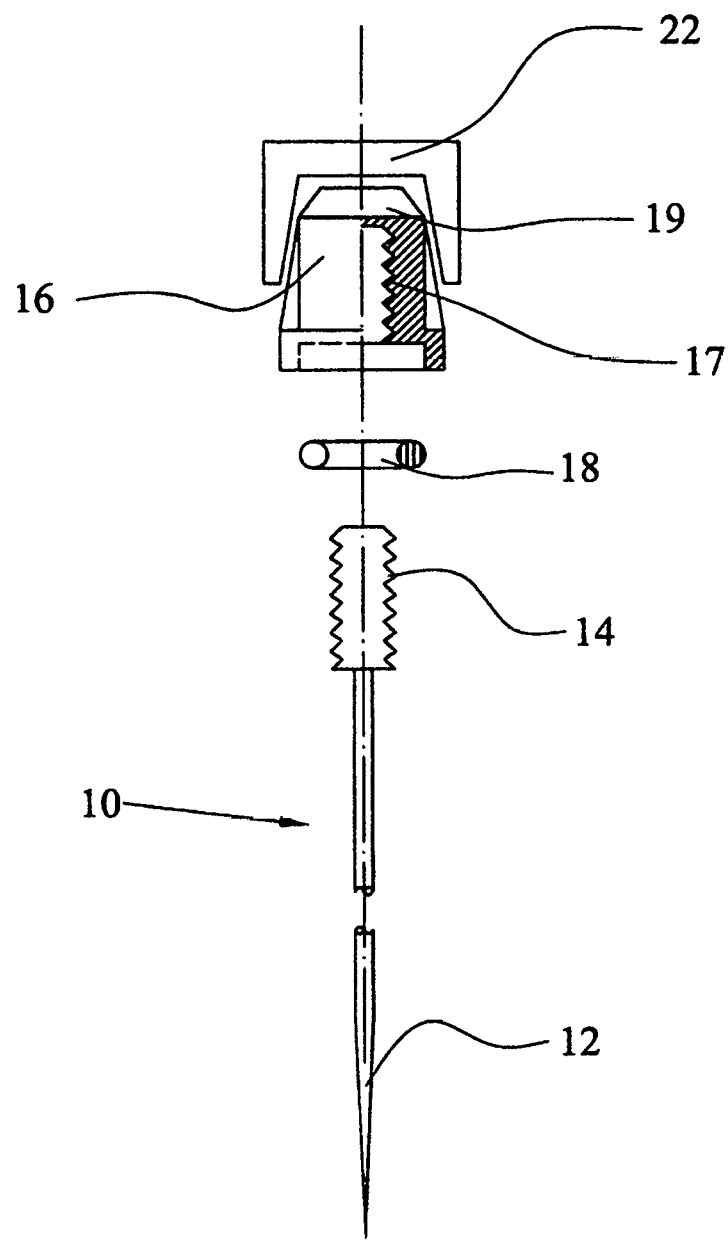
FIG. 2A is an exploded view of an acupuncture needle assembly, according to some embodiments of the invention.

FIG. 2A illustrates a schematic exploded view illustrating the needle 10, including distal beveled portion 12 and needle body with threaded outer diameter 14. O-ring 18, needle-securing element 16 with internal threaded portion 17, and fixator cup 22 are also shown. Locked nut is not shown for clarity.

FIGS. 3A-B schematically highlight the interrelationship between fixator cup 22 and skin overlaying component or butterfly 26. As shown in the cross-sectional schematic view of FIG. 3A, the butterfly 26 has two sides: a first side 28 that overlays the skin and fixator cup 22 and a second side 30 preferably configured for attachment to another surface. In a preferred embodiment, the second side 30 of the skin overlaying component 26 includes hook-and-loop fastener material, such as Velcro. FIG. 3B is a view as indicated from arrows 3A-3A shown in FIG. 3A. Fixator cup 22 and skin overlaying component 26 are illustrated.

Figure 4B:
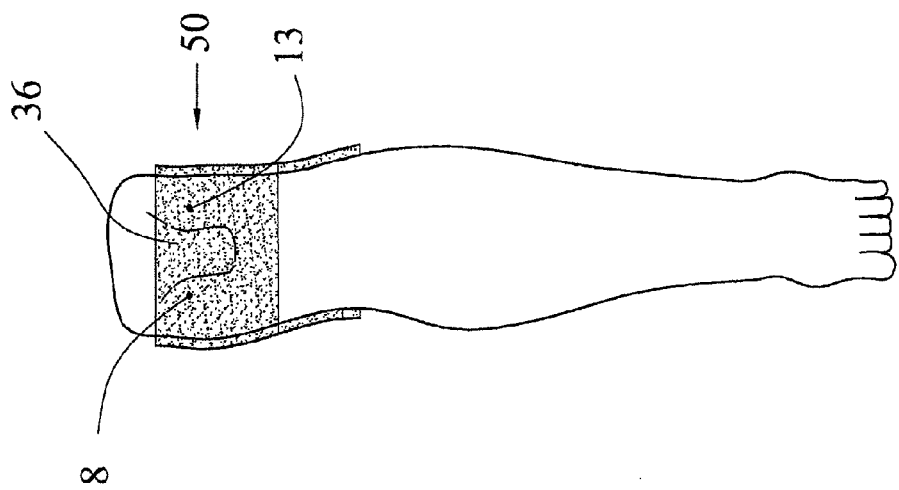
FIGS. 4A-B illustrates how the Velcro strap is used to bind the three acupuncture points: Bladder 40, Stomach 35 together with the Special Point (S145), Hsiyen or "the Eye of the Knee". These three acupuncture points are connected to the negative terminals of the electronic stimulator.
Figure 4A:
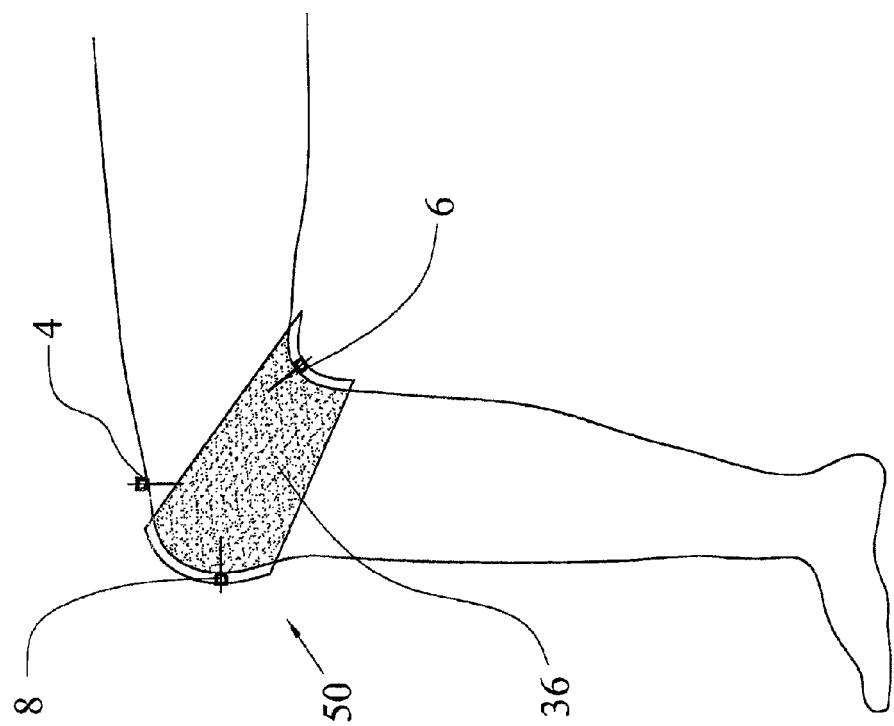

FIGS. 4A-B illustrate possible needle placements suitable for analgesia, cartilage repair and regeneration in the knee joint 50. FIG. 4A is a schematic lateral view, while 4B is an anterior-posterior view of the knee 50. The points may be selected or modified according to the desired clinical result. The depicted shaded band 36 represents a fastening element, which may be a strap with hook-and-loop fastener material in some embodiments, that can be used to bind the selected acupuncture points: "Bladder 40" 6, "Stomach 35" 13 together with the Special Point "Hsiyen (S145)" or "the Eye of the Knee" 8. These needles at the selected acupuncture points can be connected to the electronic stimulator, such as at the negative terminals.

Figure 5A:
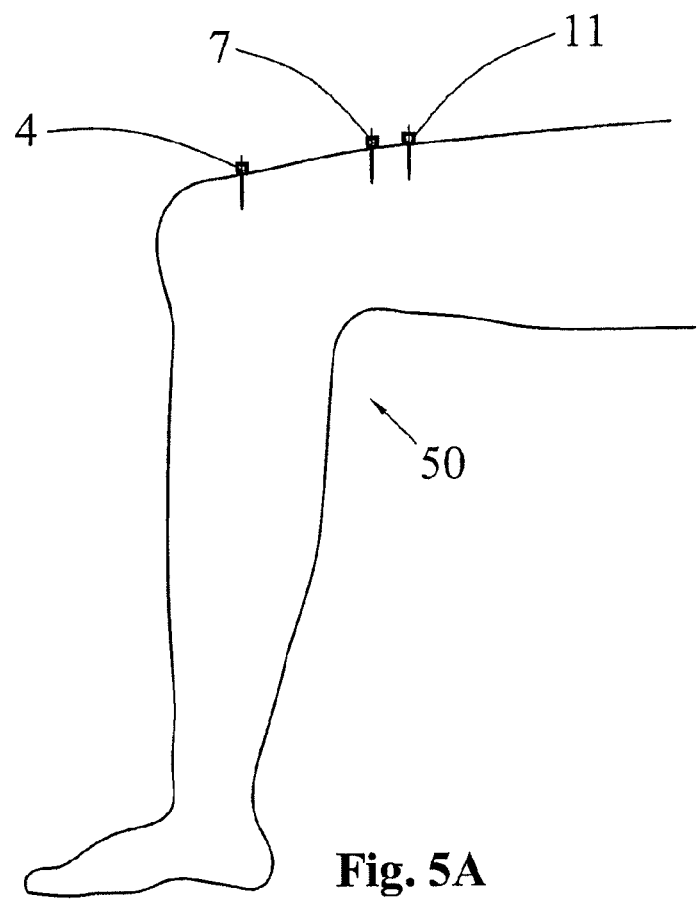
FIGS. 5A-B illustrates how the Velcro strap is used to bind the three acupuncture points: Spleen 10, Stomach 34 and the Special Point (S156) Heting or "the Crown of the Crane". These three acupuncture points are connected to the positive terminals of the electronic stimulator.
Figure 5B:
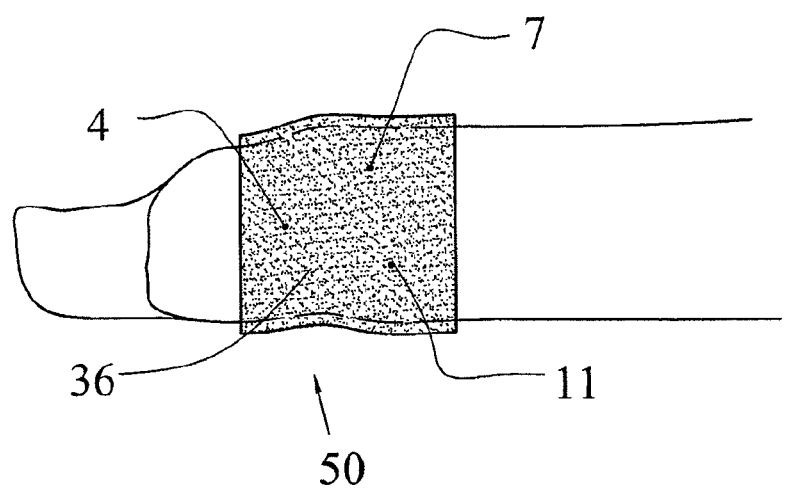

FIG. 5A further illustrates that acupuncture needles are inserted into the acupuncture points: "Stomach 34" 11, "Spleen 10" 7 and "Heting point (S156)" 4. As noted above, the exact anatomical locations of these points will be apparent to those skilled in the art. FIG. 5B illustrates a fastening strap 36 that can be used to fix the system in place, as elaborated upon in FIG. 6. In another embodiment, the system could be fixed in place by a custom designed orthotic created by one skilled in the art.

Figure 6:
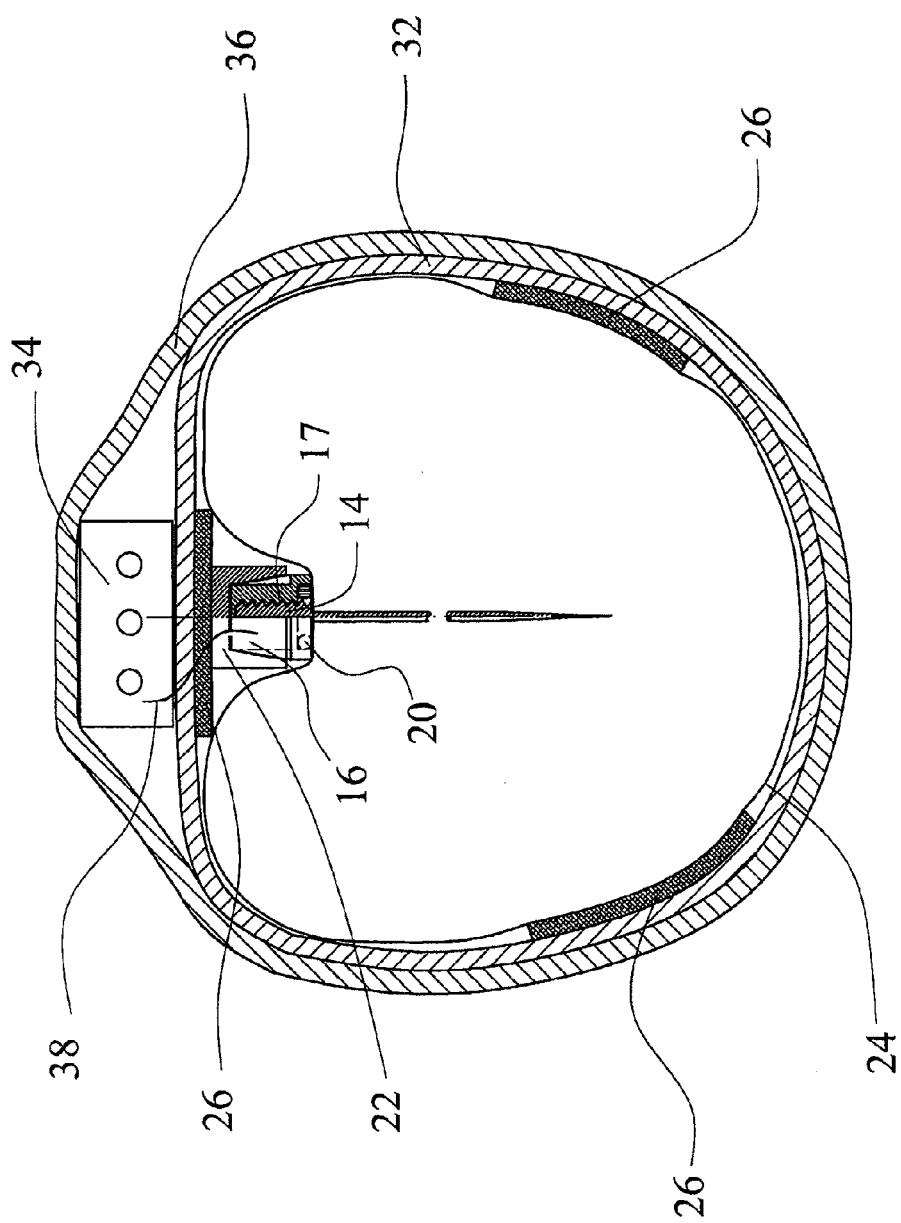
FIG. 6 shows how the electronic stimulator is attached to the double-sided Velcro by the one-sided Velcro.

FIG. 6 schematically illustrates a securable electrical acupuncture system. Shown is a winged plastic or "butterfly" skin overlaying component 26 with a preferably tapered fixation cup 22 on the first side 28 and hook-and-loop fastener material 31 on the second side 30. The tapered fixation cup 22 is most preferably press-fitted to the complementary reverse tapered end of the needle-securing component 16 with female internal-threaded portion 19 while butterfly 26 is bent to conform to the contour of the skin 24 with the side 30 having fastener material, that is most preferably hook-and-loop fastener material, exposed. A first strap 32 that preferably has hook-and-loop fastener material on both sides of the first strap 32 can be wrapped around the skin overlaying component 26 to snugly secure a portion of the system. As shown, an electrical stimulator 34 is preferably at least partially covered with fastener material, such as hook-and-loop fastener material and is preferably positioned between the first strap 32 with a double-sided hook-and-loop fastener material and a second strap 36 that preferably has hook-and-loop fastener material on a single side only. The entire system can be secured when the second strap 36 with a single side of hook-and-loop fastener material that securely positions the stimulator 34 between the second strap 36 and the first strap 32.

One of ordinary skill in the art will readily appreciate that a wide variety of fastening materials can be substituted for hook-and-loop fastener material for any or all of the disclosed components. Such fastening materials include, for example, snap fasteners, button fasteners, adhesives, tapes, buckle fasteners, locks, magnetic fasteners, custom made orthotics, and the like.

In some embodiments, the electrical stimulator 34 can have the following settings: 0-5 milliamp current, 0-18V voltage, 1-100 Hz frequency, 1-99% duty cycle. The pulse waveform is preferably square; however, other morphologies such as triangular, sinusoidal, sawtooth, spike, j-spike, and the like can also be used depending on the desired clinical result. The electrical stimulator 34 is preferably battery powered; however, the stimulator 34 could also be attached to AC or DC current in other embodiments. The battery may be rechargeable. The electrical stimulator 34 preferably includes a conduit 38 that is operably connected to the needles 10. In other embodiments, the conduit 38 may be operably connected to the fixator cup 22 or needle-securing element 16 as well in the embodiments whether these are made of a material configured to conduct electricity to the needles 10.

However, it is to be understood that the above construction is only an idealization for ease of illustration, and in reality any of the components could vary in any one or more or any combination of size, shape, size distribution, shape distribution, or other geometric or orthotic characteristics.

Methods and Method of Use

Disclosed herein is a method of treating a patient involving the steps of providing a percutaneous acupuncture system that can involve electrical stimulation or other electromagnetic forms for stimulation. The system can include one, two, three, four, five, six, seven, eight, or more needles, such as those needles described herein, percutaneously implanting the needles at a desired clinical anatomical location on the body, and securing the needles in place using one or more fastening components. The method can also include the steps of providing an electrical stimulator component, and stimulating one or more needles to promote, for example, analgesia, growth or healing of bone, cartilage, muscle, ligament, skin, or other tissues or organs.

Although described primarily herein as needles, the invention includes a variety of electrodes of various shapes that can be implanted percutaneously. Any of a variety of electrodes capable of delivering current to tissue can be used, for example, disc electrodes, spherical electrodes, wire electrodes, electrically conductive filaments or fibers that may be woven or nonwoven, metals, electrically conductive polymers, and the like as one of ordinary skill in the art would appreciate.

The metallic components of the system, e.g., the acupuncture needle 10 with threaded shank 14, the needle-securing component with threaded inside diameter 16 and the press-fit fixator cup 22 are made of biocompatible material, e.g., surgical stainless steel, titanium, or Vitalium®. The method of acupuncture needle insertion can be done manually without guide tube assistance, through a guide tube, or by any other method known in the art. The choice of the acupuncture point for needle fixation is at the discretion of the clinician.

The electrodes can be implanted anywhere appropriate in the body to any appropriate depth, depending on the desired clinical result. In some embodiments, the electrodes can be implanted to a depth of at least about 1, 2, 3, 4, 5, 7, 10, 15, 20, 25, 30, 40, 50, 60, 70, or more millimeters under the epidermis. The electrodes can be implanted intradermally, subcutaneously, intramuscularly, intraarticularly or other regions of the joint, into an organ, or other location desired by the practitioner. In some embodiments, the electrodes can be implanted in a desired location and then are stimulated wirelessly using, for example, external RF energy.

The continual or nearly continual electro-acupunctural stimulation system can be applicable to all joints, organ systems, and tissues where acupuncture needle(s) and/or an electrical field can be shown to produce analgesia, repair and/or regeneration of cartilage, muscle, ligament, skin, or other tissues or organs. In musculoskeletal diseases such as osteoarthritis of any joint, for example, joints of the cervical, thoracic, lumbar, or sacral spine; hip, knee, ankle, wrist, shoulder, hand, foot, temporomandibular, or other joints with pain and/or cartilage deterioration this methodology can be used for therapeutic effect. The systems disclosed herein can also be used to treat various diseases including acute and chronic musculoskeletal pain, rheumatoid arthritis, systemic lupus erythematosus, neuropathic pain disorders, fibromyalgia, dry macular degeneration, and the like. The systems and methods can be used to specifically treat hip osteoarthritis by providing analgesia and/or tissue regeneration and repair; hand and foot osteoarthritis by providing analgesia and/or tissue regeneration and repair; degenerative spinal disc disease by providing analgesia and/or tissue regeneration and repair; and eye tissue stabilization and repair (e.g., dry macular degeneration).

In one embodiment, a patient with a disease to be treated, such as osteoarthritis of the knee, is selected. A general overall health assessment for electrotherapy, a focused gait examination, and a Visual Analog Scale (VAS) pain assessment is conducted to better assess the patient's pre-treatment pain. The patient can receive diagnostic bi-planar X-rays and/or Tessler 7 magnetic resonance imaging (MRI) exams with body weight preload. If the patient is determined to be a suitable candidate, treatment is commenced by inserting at least one needle into each of the following six acupuncture points on the knee, for the treatment of knee osteoarthritis: "Heting (S156)" 4, "Spleen 10" 7, "Stomach 34" 11, "Bladder 40" 6, "Stomach 35" 13, and "Hsiyen (S145)" 8, as illustrated and discussed in connection with FIGS. 1A-1B. In one embodiment, the needles at points "Heting (S156)" 4, "Spleen 10" 7, and "Stomach 34" 11 serve as positive electrodes. The needles at points "Stomach 34" 11, "Bladder 40" 6, "Stomach 35" 13, and "Hsiyen (S145)" 8 serve as negative electrodes.

The needles are operably connected to an electrical stimulator 34. The power of the stimulator is then increased to a threshold level of sensation by the patient, and then decreased to a sub-sensory level for patient comfort, as well as potentially advantageously promoting analgesia and cartilage regrowth and/or remodeling. The practitioner will be able to determine with an appropriate treatment duration depending on the desired clinical result and patient progress through regular serial follow-up visits, physical examinations, pain assessments, radiographs and/or MRIs.

In other embodiments, any variety of combination or subcombinations of the points "Heting (S156)" 4, "Spleen 10" 7, "Stomach 34" 11, "Bladder 40" 6, "Stomach 35" 13, and "Hsiyen (S145)" 8 can be used as electrode insertion sites, with either negative or positive polarity depending on the desired clinical result. For example, a system may include electrodes placed at the aforementioned six points with one positive and five negative electrodes, two positive and four negative electrodes, three positive and three negative electrodes, four positive and two negative electrodes, or five positive and one negative electrodes. Furthermore, the method could include implanting electrodes at just one, two, three, four, or five of these points. Moreover, the method could include implanting electrodes at any number of these points in addition to other anatomical points as would be appreciated by one of ordinary skill in the art.

In some embodiments, such as in a monopolar system, one of the electrode with a certain polarity, such as a negative polarity, can be external to the skin, such as an externally conductive plate, strip, or wire that is held against the patient's skin, while one or more of the implanted electrodes with a different polarity, such as a positive polarity, are percutaneously implanted as described above.

In some embodiments, the energy parameters can be modified from those disclosed in U.S. Pat. No. 5,273,033 to Hoffman or U.S. Pat. No. 7,200,444 to Gavronsky et al., both of which are hereby incorporated by reference in its entirety. In some embodiments, the electrical stimulator power remains above a threshold sensory level during treatment. In other embodiments, the stimulator power remains sub-sensory throughout the time the needles are operably connected to the stimulator. In still other embodiments, the stimulator power can cycle between sensory and sub-sensory power levels during treatment. Candidates for total joint replacement may benefit by undergoing nearly continuous stimulation over an extended period of time. In some embodiments, the system is left in place for 2-5 weeks as a therapeutic trial before contemplating more invasive surgical procedures. In some embodiments, the system can be implanted percutaneously for at least about 1, 2, 3, 5, 7, 10, 14, 21, 28, 35, 42, 60, 90, 120 or more days depending upon the desired clinical result. The various fastening mechanisms disclosed herein can advantageously assist in providing secure implantation of the system for extended periods of time The electrical stimulator may be turned on continuously for 24 hours each day. However, in some embodiments, it may be preferable that the electrical stimulator be only activated for only a portion of each day, for example, at least about 1, 2, 3, 4, 6, 8, 10, 12, 14, 16, 18, 20 hours or more each day, and not be active when the patient is more actively moving the area to be treated in activities such as standing, walking, bathing, or the like. In some embodiments, the electrical stimulator may have a mercury switch automatically that turns off the stimulator when the patient stands and resumes stimulation when the patient is seated or in a recumbent position. In other embodiments, the stimulator can be turned on or off manually.

In other embodiments, the system can be implanted without the electrical stimulator component, to provide the benefits of acupuncture without electrical stimulation, depending on the desired clinical result.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For the disclosed methods, the steps need not necessarily be performed sequentially.

What is claimed is:

1. A securable percutaneous acupunctural system comprising:
    at least one needle comprising an elongate body, proximal end, and distal end, the needle having a fastener component disposed on the elongate body, wherein the needle is percutaneously inserted into a treatment site;
    a needle-securing element configured to lock the implanted needles in situ, wherein the needle-securing element is placed over the proximal end of the needle, and wherein the needle is retained in a desired anatomical point;
    wherein the elongate body of the needle comprises a male screw threaded portion;
    wherein the needle has a diameter of between 20 to 40 gauge, and the needle is inserted into a guide tube and inserted 3 to 5 mm through the skin into the desired anatomical point, the guide tube is then removed;
    wherein the needle-securing element comprising a female-threaded portion that is adapted to accommodate the male threaded portion of the needle; and
    wherein the needle-securing element has a proximal end, the proximal end of the needle-securing element has a press-fit outer surface;
    a fixator cup having a press-fit surface on its inner surface configured to attach to the press-fit outer surface of the needle-securing element; and
    a component having two sides configured to overlay the skin, wherein a first side overlays the fixator cup and the skin.

2. The system of claim 1, wherein the needles have a diameter of between about 30 to 34 gauge.

3. The system of claim 1, wherein the needles have a length of between about 8 mm to 2.5 cm.

4. The system of claim 1, wherein an outer surface of the cup is tied or soldered with a ring, which is connected to an insulated wire.

5. The system of claim 4, wherein the wire is connected to one of the positive or negative leads of a jack, the jack having both the positive and negative leads connected to it; the jack operably connected to an output port of an electronic stimulator.

6. The system of claim 1, further comprising an O-ring at a distal end of the needle-securing element, wherein at least a portion of the O-rang is coated with an antimicrobial agent.

7. The system of claim 1, further comprising a locked nut in between the fixator cup and the needle-securing element, wherein the needle-securing element is screwed in place and closed with the locked nut.

8. The system of claim 1, wherein a second side of the component is configured for attachment to another surface.

9. The system of claim 8, wherein the second side of the component comprises hook-and-loop fastener material.

* * * * *